United States Patent [19]

Mueller

[11] 4,045,442

[45] Aug. 30, 1977

[54] 1-(SUBSTITUTED AMINO)ALKANOYL-2-(DIBENZOXAZE-PINE-10-CARBONYL)HYDRAZINES AND DERIVATIVES THEREOF

[75] Inventor: Richard A. Mueller, Northbrook, Ill.

[73] Assignee: G. D. Searle & Co., Chicago, Ill.

[21] Appl. No.: 646,686

[22] Filed: Jan. 5, 1976

[51] Int. Cl.$^2$ .......................................... C07D 413/12
[52] U.S. Cl. ............................. 260/293.58; 424/244; 424/248.54; 424/250; 424/267; 424/269; 424/274; 260/268 TR; 260/326.36; 260/333; 548/336; 260/243.3
[58] Field of Search ............... 260/333, 293.58, 326.36

[56] References Cited

U.S. PATENT DOCUMENTS

| | | | |
|---|---|---|---|
| 3,534,019 | 10/1970 | Coyne et al. | 260/239 |
| 3,624,104 | 10/1969 | Cusic et al. | 260/333 |
| 3,953,469 | 4/1976 | Krapcho | 260/333 |

OTHER PUBLICATIONS

Chemical Abstracts, vol. 77, abst. no. 164,780v (1972), (abst. of German Offen. 2,213,809).

Primary Examiner—John D. Randolph
Attorney, Agent, or Firm—John J. McDonnell

[57] ABSTRACT

The reaction of 1-(halo/cyano/sulfonyloxy)alkanoyl-2-(dibenzoxazepine-10-carbonyl)hydrazines with an amine affords the corresponding 1-(substituted amino-)alkanoyl-2-(dibenzoxazepine-10-carbonyl)hydrazines which compounds are useful anti-inflammatory or anti-diarrheal agents.

10 Claims, No Drawings

1-(SUBSTITUTED AMINO)ALKANOYL-2-(DIBENZOXAZEPINE-10-CARBONYL)HYDRAZINES AND DERIVATIVES THEREOF

The present invention is concerned with compounds of the formula:

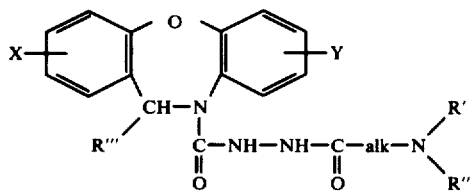

wherein X and Y represent hydrogen, halogen, lower alkyl having 1–7 carbon atoms, or trifluoromethyl; alk represents lower alkylene having 1–6 carbon atoms; R' and R" represent lower alkyl having 1–6 carbon atoms or R' and R" together With N represents an azamonocyclic ring wherein the azamonocyclic ring is selected from the group consisting of imidazolyl, pryrrolidino, 2,5-dimethylpyrrolidino, hexahydroazapine, piperidino, 4-ethoxycarbonyl-4-phenylpiperidino, 4-hydroxy-4-phenylpiperidino, 4-carboxy-4-phenylpiperidino, morpholino, piperazinyl, 4-methylpiperazinyl, or R' and R" together with N represent an azabicyclic ring wherein the azabicyclic ring is 2-azabicyclo[2.2.2]oct-2-yl; and R''' represents hydrogen or lower alkyl having 1–4 carbon atoms. Halogen refers to fluorene, chlorine, bromine, and iodine and lower alkyl having 1–6 carbon atoms refers to methyl, ethyl, propyl, butyl, pentyl, hexyl and branched chain isomers thereof. Those skilled in the pharmaceutical arts will recognize the equivalency of the free bases of the present invention and pharmaceutically acceptable acid addition salts thereof, such as acid addition salts of sulfuric, phosphoric, hydrochloric, hydrobromic, hydroiodic, sulfamic, citric, lactic, maleic, malic, succinic, lactoic, cinnamic, acetic, benzoic, gluconic, ascorbic, and related acids.

Embodiments of the present invention of the formula

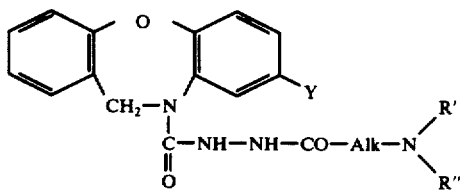

wherein Y is hydrogen, halogen or trifluoromethyl and Alk and R' and R" are as earlier defined are preferred and of this embodiment Alk equal to —(CH$_2$)$_4$— is the most preferred.

Embodiments of the formula

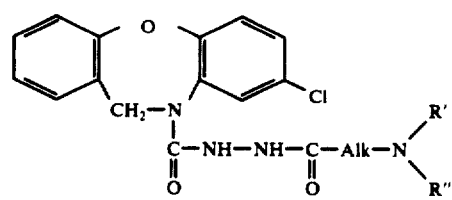

wherein Alk and R' and R" alone and in combination with N are as previously described are preferred.

Embodiments of the formula

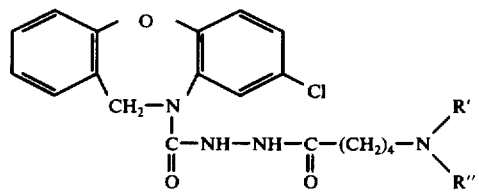

wherein R' and R" alone and in combination with N are as previously described are especially preferred. In this latter formula the embodiment represented by R' and R" equal to lower alkyl having 1–6 carbon atoms is exemplified by 1-(5-dipropylaminopentanoyl)-2-(8-chloro-10,11-dihydrodibenz[b,f][1,4]oxazepine-10-carbonyl)hydrazine.

Embodiments of the latter formula wherein R' and R" together with N represents an azamonocyclic ring are exemplified by 1-(5-pyrrolidinopentanoyl)-2-(8-chloro-10,11-dihydrodibenz[b,f][1,4]oxazepine-10-carbonyl)hydrazine, 1-(5-pyrrolidinopentanoyl)-2-(8-chloro-10,11-dihydrodibenz[b,f][1,4]oxazepine-10-carbonyl)hydrazine, 1-(5-morpholinopentanoyl)-2-(8-chloro-10,11-dihydrodibenz[b,f][1,4]oxazepine-10-carbonyl)hydrazine, 1-(5-imidazolylpentanoyl)-2-(8-chloro-10,11-dihydrodibenz[b,f][1,4]oxazepine-10-carbonyl)hydrazine, 1-[5-(4-methylpiperazinyl)pentanoyl]-2-(8-chloro-10,11-dihydrodibenz[b,f][1,4]oxazepine-10-carbonyl)hydrazine.

Embodiments of the latter formula wherein R' and R" together with N represent an azabicyclic ring are exemplified by 1-[5-(2-azabicyclo[2.2.2]oct-2-yl)pentanoyl]-2-(8-chloro-10,11-dihydrodibenz[b,f][1,4]oxazepine-10-carbonyl)hydrazine.

Embodiments of the formula

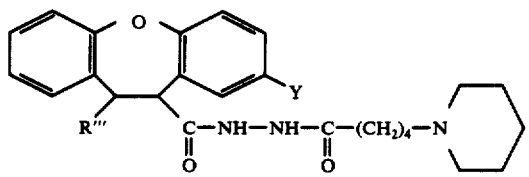

wherein Y is hydrogen, halogen, lower alkyl having 1–7 carbon atoms, or trifluoromethyl and R''' is lower alkyl having 1–4 carbon atoms are preferred with 1-(5-piperidinopentanoyl)-2-(3-chloro-11-methyl-10,11-dihydrodibenz[b,f][1,4]oxazepine-10-carbonyl)hydrazine being the most preferred member.

Compounds of the present invention are prepared according to the following reaction scheme:

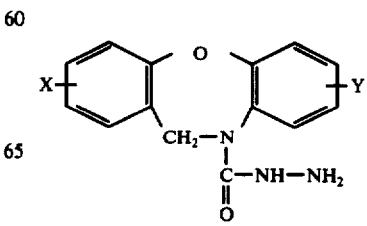

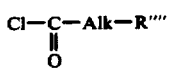

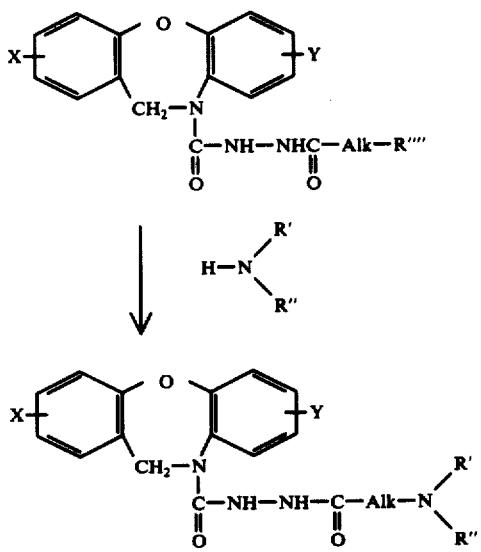

wherein X, Y, Alkyl, R', and R" are as previously defined and R"" is chloride, bromide, iodide, cyanide, or sulfonyloxy. Appropriate hydrazines are described in U.S. Pat. No. 3,534,019. As a specific most preferred example, 8-chloro-10,11-dihydrodibenz[b,f][1,4]oxazepine-10-carboxylic acid hydrazide (U.S. Pat. No. 3,534,019) is contacted with 5-chloropentanoyl chloride to afford 1-(5-chloropentanoyl)-2-(8-chloro-10,11-dihydrodibenz[b,f][1,4]oxazepine-10-carbonyl)hydrazine. Reaction of the latter substance with pyrollidine results in 1-(5pyrrolidinopentanoyl)-2-(8-chloro-10,11-dihydrodibenz[b,f][1,4]oxazepine-10-carbonyl)hydrazine.

Compounds of the present invention wherein R''' represents lower alkyl are prepared according to the following scheme:

pounds of this invention by the previously set out sequence of reactions.

Thus following procedures set out in U.S. Pat. No. 3,534,019 compounds of the formula

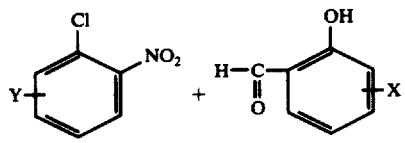

may be condensed into an appropriately substituted azepine and in turn converted to the appropriately substituted hydrazine derivative. Thus cross reaction of

| A | B |
|---|---|
| 2,4-dichloronitrobenzene | 2-hydroxybenzaldehyde |
| 2-chloro, 4-bromonitrobenzene | 2-hydroxy-5-methylbenzaldehyde |
| 2-chloro, 4-fluoronitrobenzene | |
| 2-chloro, 4-trifluoromethylnitrobenzene | 2-hydroxy-4-chlorobenzaldehyde |
| 2-chloro, 4-methylnitrobenzene | 2-hydroxy-5-bromobenzaldehyde |
| 2-chloronitrobenzene | 2-hydroxy-3-triflouromethylbenzaldehyde | provides starting materials for compounds of the present invention.

Compounds of the present invention have antidiarrheal and anti-inflammatory activity.

The anti-inflammatory properties of the instant compounds is demonstrated by their activity in an assay adapted from that described by Tonelli et al., *Endocrinology*, 77, 625 (1965) and detailed as follows:

0.1 Cubic centimeter of a phlogistic vehicle consisting of 4 parts of pyridine, 1 part of distilled water, 5 parts of diethyl ether and 10 parts of 2% Croton oil in ether (v/v) is applied topically to the right ear of each of a group of 8–10 rats, while the contralateral left ear remains untreated and serves as the control. For the determination of activity of the test compound a similar group of animals is treated with the same volume of the

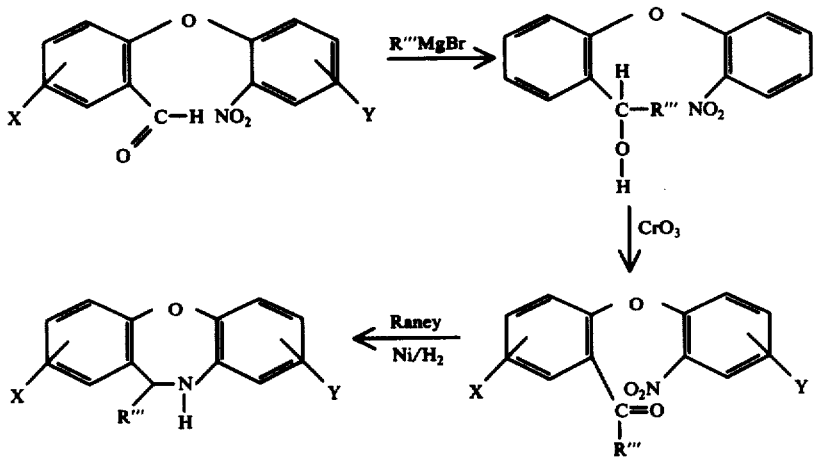

wherein X, Y, and R''' are defined as before. This 10,11-dihydrodibenz[b,f][1,4]oxazepine is converted to the corresponding 10-carboxylic acid hydrazine as described in U.S. Pat. No. 3,534,019 and, in turn, to compounds phlogistic vehicle containing 400 mcg. of the compound. In addition, a third group of animals is treated in the same manner with the same volume of the phlogistic vehicle containing 80 mcg. of a standard topical anti-inflammatory agent (hydrocortisone).

Six hours after treatment the animals are lightly etherized and both ears are removed by means of a scissors, using anatomical structures of the ears as the line of demarcation. The ears are weighed individually and the percent increase in weight of the inflamed ear as compared to the untreated contralateral ear is determined. The percent increase in ear weight of the compound treated group is then compared statistically by Wilcoxon Rank Sum Analysis with the percent increase in ear weight of the control group which received the phlogistic acid alone.

The anti-diarrheal properties of the compounds of this invention are apparent from their activity in the following assay procedure.

To groups of 10 Charles River male mice weighing 30–40 g. is administered intraperitoneally a selected dose of the test compound suspended in an aqueous medium containing 0.1% of polysorbate 80 (polyoxyethylene sorbitan mono-oleate). A constant volume of 0.1 ml/10 g. body weight of the suspension is used for each animal.

Fifteen minutes after administration of the test compound, the mice are injected intraperitoneally with 50 μg/kg body weight of prostaglandin $E_2$, the dose previously demonstrated to produce diarrhea in more than 95% of control animals. Thereafter, each mouse is placed on a disc of filter paper in an individual glass cylinder and observed for a period of 15 minutes for the presence or absence of diarrhea. The compound is tested at a variety of dosage levels until at least one dose results in protection of more than 50% of the mice. The protective dose — prD50 — is calculated by the method of D. J. Finney, "Statistical Method in Biological Assay", Chapter 17, Hafner Publishing Co., New York, 1964, using the proportion of mice protected by each dose of compound.

Thus compounds of the present invention may be combined with pharmaceutically useful prostaglandins to suppress undesirable side effects such as diarrhea.

The following examples will further illustrate the present invention. They should not be construed as limiting the invention either in spirit or in scope as modifications both in materials and methods will be apparent to those skilled in the art. In these examples temperatures are indicated in degrees Centigrade (° C.) and quantities of materials in parts by weight unless parts by volume is specifically expressed.

EXAMPLE 1

To a solution of 0.5 part of 8-chloro-10,11-dihydrodibenz[b,f][1,4]oxazepine-10-carboxylic acid hydrazide (U.S. Pat. No. 3,534,019) and 19.6 parts of acetonitrile is added 0.298 part of sodium bicarbonate followed by 0.6 part of 5-chloropentanoyl chloride. The solution is stirred for 48 hours at room temperature, after which time the solvent is removed under reduced pressure and the resulting residue is purified by recrystallization from ethyl acetate-cyclohexane to afford 1-(5-chloropentanoyl)-2-(8-chloro-10,11-dihydrodibenz[b,f][1,4]oxazepine-10-carbonyl)hydrazine, which has a melting point at about 148°–149° and is structurally represented by the following formula

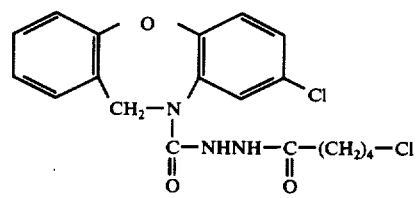

14.8 Parts of the above chloride is reacted with 7.94 g of sodium iodide in 145 parts by volume of acetone containing a catalytic amount of sodium thiosulfate. The reaction mixture is stirred in the dark and refluxed for 5 hours and allowed to stand at room temperature. The solvent is removed and the residue taken up in benzene containing 1% sodium thiosulfate. The benzene is washed with aqueous sodium chloride and dried over sodium sulfate to provide an approximately 50—50 mixture of 1-(5-iodopentanoyl)-2-(8-chloro-10,11-dihydrodibenz[b,f][1,4]oxazepine-10-carbonyl)hydrazine and the (5-chlorcpentanoyl) derivative. 8 Parts of this mixture is reacted with 1.65 parts of morpholine in 80 parts by volume of acetone for 48 hours. The acetone is removed and 10% hydrochloric acid and benzene is added to the benzene layer. The benzene layer is separated and the aqueous acid layer is made basic with 5% potassium hydroxide and then extracted with benzene. The benzene layer is washed with sodium chloride solution and dried over sodium sulfate. The solvent is removed and the residue is crystallized from ethyl acetatecyclohexane to provide 1-(5-morpholinopentanoyl)-2-(8-chloro-10,11-dihydrodibenz[b,f][1,4]oxazepine-10-carbonyl)hydrazine melting at 107°–114° C and having the following structural formula

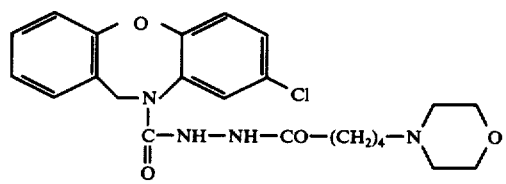

EXAMPLE 2

Following the procedure in Example 1, using equivalent quantities, and replacing morpholine with piperidine provides 1-(5-piperidinopentanoyl)-2-(8-chloro-10,11-dihydrodibenz[b,f][1,4]oxazepine-10-carbonyl)-hydrazine, melting at 126°–128° C and having the following structural formula

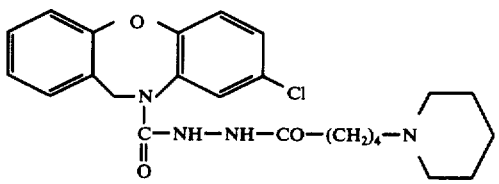

EXAMPLE 3

Following the procedure in Example 1, using equivalent quantities, and replacing morpholine with 4-methylpiperazine provides 1-[5-(4-methyl-piperizinopentanoyl)]-2-(8-chloro-10,11-dihydrodibenz[b,f][1,4]oxazepine-10-carbonyl)hydrazine, melting at 138°–140° C and having the following structural formula

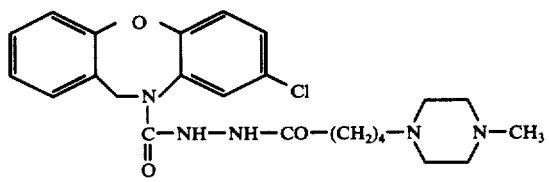

EXAMPLE 4

Following the procedure in Example 1, using equivalent quantities, and replacing morpholine with imidazole provides 1-(5-imidazolylpentanoyl)-2-(8-chloro-10,11-dihydrodibenz[b,f][1,4]oxazepine-10-carbonyl)-hydrazine, melting at 164°–166° C and having the following structural formula

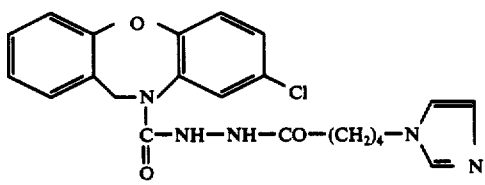

EXAMPLE 5

Following the procedure in Example 1, using equivalent quantities, and replacing morpholine with dipropylamine provides 1-(5-dipropylaminopentanoyl)-2-(8-chloro-10,11-dihydrodibenz[b,f][1,4]oxazepine-10-carbonyl)hydrazine as an oil having the following structural formula

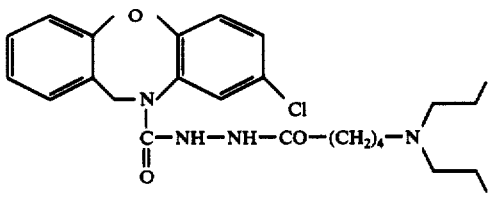

EXAMPLE 6

Following the procedure in Example 1, using equivalent quantities, and replacing morpholine with 4-ethoxycarbonyl-4-phenylpiperidine provides 1-[5-(4-ethoxycarbonyl-4-phenylpiperidinopentanoyl)]-2-(8-chloro-10,11-dihydrodibenz[b,f][1,4]oxazepine-10-carbonyl)-hydrazine, melting at 105°–108° C. and having the following structural formula

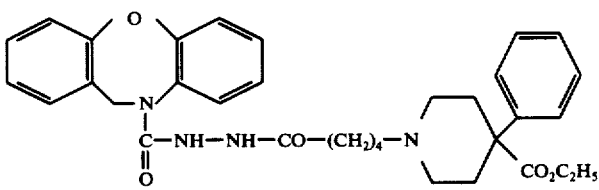

EXAMPLE 7

Following the procedure in Example 1, using equivalent quantities, and replacing morpholine with pyrolidine provides 1-(5-pyrrolidinylpentanoyl)-2-(8-chloro-10,11-dihydrodibenz[b,f][1,4]oxazepine-10-carbonyl)-hydrazine, melting at about 133°–135° C. and having the following structural formula

EXAMPLE 8

Following the procedure in Example 1, using equivalent quantities, and replacing morpholine with 2,5-dimethylpyrolidine provides 1-[5-(2,5-dimethylpyrrolidinylpentanoyl)]-2-(8-chloro-10,11,-dihydrodibenz[b,f][1,4]-oxazepine-10-carbonyl)hydrazine as an oil having the following structural formula

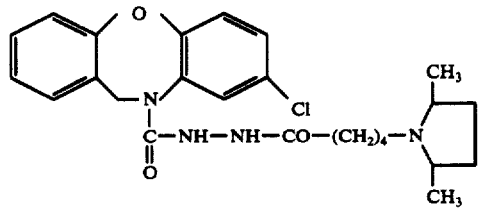

EXAMPLE 9

Following the procedure in Example 1, using equivalent quantities, and replacing morpholine with methylphenethylamine provides 1-(5-methylphenethylaminopentanoyl)-2-(8-chloro-10,11-dihydrodibenz[b,f][1,4]oxazepine-10-carbonyl)hydrazine as an oil having the following structural formula

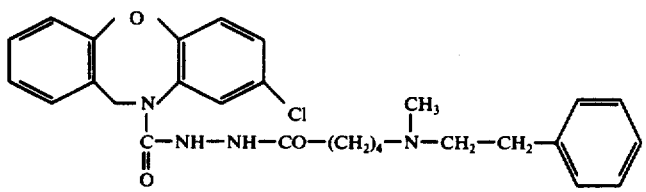

EXAMPLE 10

Following the procedure in Example 1, using equivalent quantities, and replacing morpholine with 2-azabicyclo[2.2.2]octane provides 1-[5-(2-azabicyclo[2.2.2]-oct-2-yl pentanoyl)]-2-(8-chloro-10,11-dihydrodibenz[b,f][1,4]oxazepine-10-carbonyl)hydrazine having the following structural formula

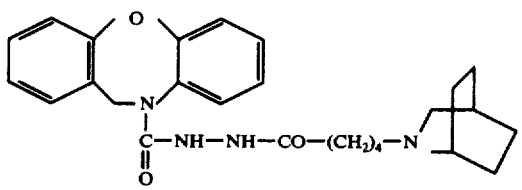

EXAMPLE 11

When an equivalent quantity of 5-chloro-3-methylpentanoyl chloride and an equivalent quantity of potassium carbonate, as the acid acceptor, are substituted in the procedure of Example 1, there is obtained, after recrystallization from cyclohexane, 1-(5-chloro-3-methylpentanoyl)-2-(8-chloro-10,11-dihydrodibenz[b,f][1,4]oxazepine-10-carbonyl)hydrazine, melting at about 125°-128° C. This material is reacted with piperidine as set out in Example 2 to provide 1-(5-piperidino-3-methylpentanoyl)-2-(8-chloro-10,11-dihydrodibenz[b,f][1,4]oxazepine-10-carbonyl)hydrazine, melting at 108°-111° C and having the following structural formula

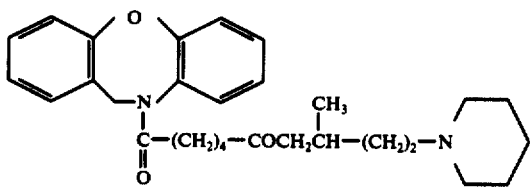

EXAMPLE 12

When the procedure of Example 1 is carried out, substituting equivalent quantities of chloroacetic anhydride as the acylating agent and sodium bicarbonate as the acid acceptor, there is produced 1-chloroacetyl-2-(8-chloro-10,11-dihydrodibenz[b,f][1,4]oxazepine-10-carbonyl)hydrazine, melting at about 174°-176° C. 3.66 Parts of this material is dissolved in 100 parts by volume of benzene and reacted with 4 parts of sodium iodide and 4 parts of pyrrolidine by procedures set out in Example 1 to provide 1-pyrrolidinylacetyl-2-(8-chloro-10,11-dihydrodibenz[b,f][1,4]oxazepine-10-carbonyl)-hydrazine, melting at 180°-182° C. and having the following structural formula

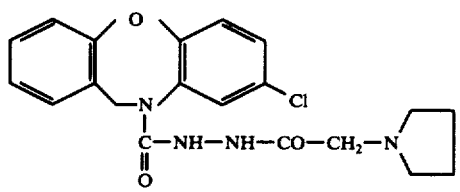

Using equivalent quantities of 4-hydroxy-4-phenylpiperidine in place of pyrrolidine provides 1-(4-hydroxy-4-phenylpiperidinoacetyl)-2-(8-chloro-10,11-dihydrodibenz[b,f][1,4]oxazepine-10-carbonyl)hydrazine having the following structural formula

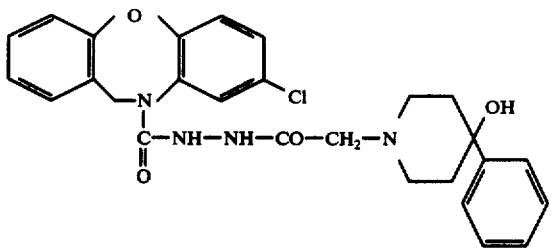

EXAMPLE 13

Substituting 8-trifluoromethyl-10,11-dihydrodibenz[b,f][1,4]oxazepine-10-carboxylic acid hydrazide (U.S. Pat. No. 3,534,019), sodium carbonate and 5-chloropentanoyl chloride in the procedure of Example 1, there is produced 1-(5-chloropentanoyl)-2-(8-trifluoromethyl-10,11-dihydrodibenz[b,f][1,4]oxazepine-10-carbonyl)hydrazine. This compound melts at about 121.5°-123.5° C and is represented by the following structural formula

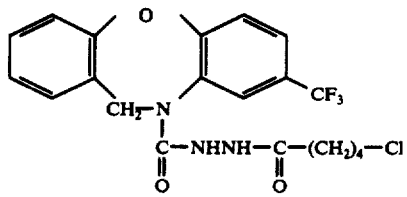

Following the procedure in Example 1 this material is reacted with morpholine to provide 1-(5-morpholinopentanoyl)-2-(8-trifluoromethyl-10,11-dihydrodibenz[b,f][1,4]oxazepine-10-carbonyl)hydrazine having the following structural formula

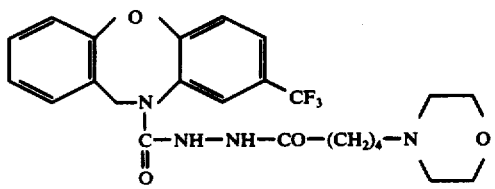

EXAMPLE 14

Substituting 10,11-dihydrodibenz[b,f][1,4]oxazepine-10-carboxylic acid hydrazide (U.S. Pat. No. 3,534,019), sodium carbonate and 5-chloropentanoyl chloride in the procedure of Example 1, there is produced 1-(5-chloropentanoyl)-2-(8-trifluoromethyl-10,11-dihydrodibenz[b,f][1,4]-oxazepine-10-carbonyl)hydrazine. This compound is represented by the following structural formula

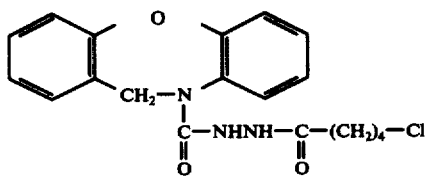

Following the procedure in Example 1 this material is reacted with morpholine to provide 1-(5-morpholinopentanoyl)-2-(10,11-dihydrodibenz[b,f][1,4]oxazepine-10-carbonyl)hydrazine having the following structural formula

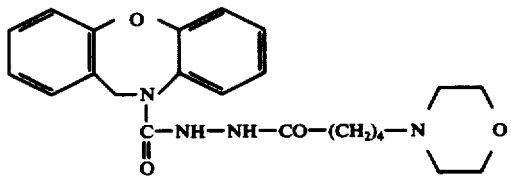

EXAMPLE 15

200 Parts of 2-chloro-4-fluoronitrobenzene is heated to 160° C. and stirred and 160 parts of the potassium salt of 5-methyl salicylaldehyde is added over a 30 minute period. After an exothermic reaction the mixture is heated at 150° C. for 1 hour. The mixture is cooled, ice and water are added, and it is then extracted with ether. The ether is filtered to remove insoluble material and the resultant solution is dried over sodium sulfate. The ether solvent is then evaporated and the residual oil is recrystallized from a mixture of hexane and benzene to provide 2-(2-nitro-4-fluorophenoxy)-5-methylbenzaldehyde having the following structural formula

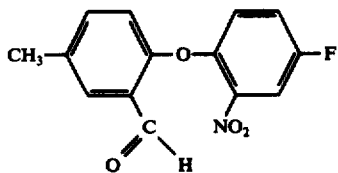

A solution of 55 parts of this material is placed in 800 parts of ethanol and hydrogenated over Raney nickel catalyst at room temperature and atmospheric pressure. When hydrogen uptake ceases the catalyst is removed by filtration and the ethanol solvent is removed. The residue is then dissolved in 500 parts by volume of hexane, filtered, and cooled to provide 2-methyl-8-fluoro-10,11-dihydrodibenz[b,f][1,4]oxazepine.

13 Parts of phosgene in 45 parts of toluene is stirred at 5°-10° C. and 70 parts of ether is added. This is followed by the addition of a solution of 18.9 parts of the above oxazepine and 7.2 parts of triethylamine in 140 parts of ether. After the addition is complete, the mixture is stirred for 2 hours and then filtered and the solvent is evaporated from the filtrate. The residue is dissolved in 200 parts by volume of hot hexane and this mixture is then filtered and cooled to provide 8-fluoro-2-methyl-10,11-dihydrodibenz[b,f][1,4]oxazepine-10-carbonyl chloride. To a solution of 7.3 parts of 100% hydrazine hydrate in 40 parts of ethanol there is added, at 5°-10° C. with stirring, a solution of 13.0 parts of the above oxazepine-10-carbonyl chloride in 200 parts by volume of 1:1 ether-methylene chloride solution. When the addition is complete, the mixture is allowed to warm to room temperature and stirred for 1 hour. The mixture is then filtered and the solvent is evaporated from the filtrate. The resultant residue is dissolved in chloroform and the chloroform solution is washed with water and dried over magnesium sulfate. Removal of the chloroform and crystallization provides 2-methyl-8-fluoro-10,11-dihydrodibenz[b,f][1,4]oxazepine-10-carboxylic acid hydrazide. Following the procedure set out in Example 1 this hydrazide is converted to 1-(5-morpholinopentanoyl)-2-(8-fluoro-2-methyl-10,11-dihydrodibenz[b,f][1,4]oxazepine-10-carbonyl)hydrazine, having the following structural formula

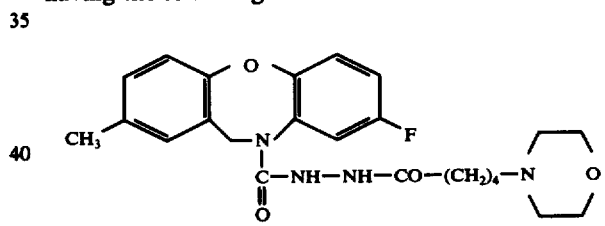

EXAMPLE 16

Following the procedure set out in Example 15 5-fluorosalicylaldehyde is reacted with 2-chloro-4-methylnitrobenzene to 1-(5-morpholinopentanoyl)-2-(8-methyl-2-fluoro-10,11-dihydrodibenz[b,f][1,4]oxazepine-10-carbonyl)hydrazine, having the following structural formula

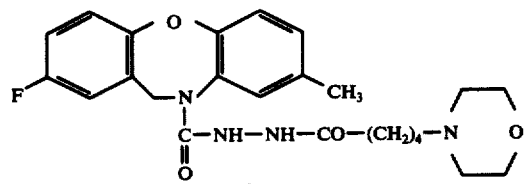

EXAMPLE 17

14.89 Parts of 2-(2-nitro-4-chlorophenoxy) benzaldehyde is dissolved in 150 parts by volume of tetrahydrofuran and cooled to −78° C. 30 Parts by volume of 2.5 molar methylmagnesium bromide in tetrahydrofuran is added over 0.5 hour in an inert atmosphere. The solution is stirred for 0.5 hour at −78° C and then allowed to warm to 0°-5° C. The reaction is quenched with 100 parts by volume of 0.01 N hydrochloric acid. The reaction is further diluted with 100 parts by volume of 1N hydrochloric acid and 200 parts by volume of water and then extracted with benzene. The benzene phase is separated, washed with water saturated sodium chloride, and dried over anhydrous sodium sulfate. The dry solution is distilled to remove solvent and provide 16.3 parts of 2-(2-nitro-4-chlorophenoxy)-11-methylbenzylalcohol.

10.5 Parts of This oil is dissolved in 100 parts by volume of acetone and cooled to 0°-5° C. 15 parts by volume of Jones reagent (from 100 parts of $CrO_3$ dissolved in 153 parts of concentrated sulfuric acid diluted with water to a final volume of 500 parts by volume) to provide 2-(2-nitro-4-chlorophenoxy)acetophenone.

Reduction with Raney nickel as described in Example 15 provides 3-chloro-11-methyl-10,11-dihydrodibenz[b,f][1,4]oxazepine. Further following the procedure set out in Examples 1 and 2, this material is successively converted to 8-chloro-11-methyl-10,11-dihydrodibenz[b,f][1,4]oxazepine-10-carbonyl chloride, 8-chloro-11-methyl-10,11-dihydrodibenz[b,f][1,4]oxazepine-10-carboxylic acid hydrazide and to 1-(5-piperidinopentanoyl)-2-(8-chloro-11-methyl-10,11-dihydrodibenz[b,f][1,4]oxazepine-10-carbonyl)hydrazine, having the following structural formula

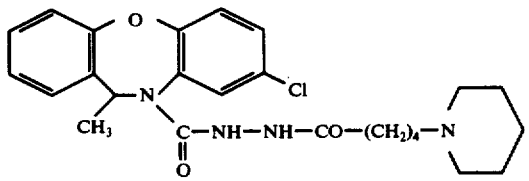

EXAMPLE 18

Following the procedure in Example 17 and replacing methylmagnesium bromide with an equivalent quantity of ethylmagnesium bromide provides 1-(5-piperidinopentanoyl)-2-(8-chloro-11-methyl-10,11-dihydrodibenz[b,f][1,4]oxazepine-10carbonyl)hydrazine, having the following structural formula

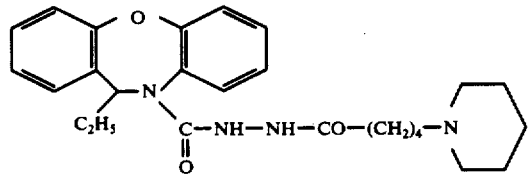

What is claimed is:
1. A compound of the formula

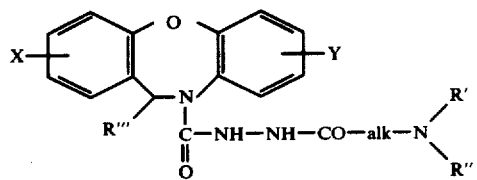

wherein X and Y represent hydrogen, halogen, lower alkyl having 1-7 carbon atoms, trifluoromethyl; alk represents lower alkylene having 1-6 carbon atoms; R' and R" together
with N represents an azamonocyclic ring wherein the azamonocyclic ring is pyrrolidino, 2,5-dimethylpyrrolidino, hexahydroazepine, piperidino, 4-ethoxycarbonyl-4-phenylpiperidino, 4-hydroxy-4-phenylpiperidino, 4-carboxy-4-phenylpiperidino, and R''' represents hydrogen or lower alkyl having 1-4 carbon atoms.

2. The compound according to claim 1 which is 1-(5-piperidinopentanoyl)-2-(8-chloro-10,11-dihydrodibenz[b,f][1,4]oxazepine-10-carbonyl)hydrazine.

3. The compound according to claim 1 which is 1-[5-(4-ethoxycarbonyl-4-phenylpiperidinopentanoyl)]-2-l-(8-chloro-10,11-dihydrodibenz[b,f][1,4]oxazepine-10-carbonyl)hydrazine.

4. The compound according to claim 1 which is 1-(5-pyrrolidinylpentanoyl)-2-(8-chloro-10,11-dihydrodibenz[b,f][1,4]oxazepine-10-carbonyl)hydrazine.

5. The compound according to claim 1 which is 1-[5-(2,5-dimethylpyrrolidinylpentanoyl)]-2-(8-chloro-10,11-dihydrodibenz[b,f][1,4]oxazepine-10-carbonyl)-hydrazine.

6. The compound according to claim 1 which is 1-(5-piperidino-3-methylpentanoyl)-2-(8-chloro-10,11-dihydrodibenz[b,f][1,4]oxazepine-10-carbonyl)hydrazine.

7. The compound according to claim 1 which is 1-pyrrolidinylacetyl-2-(8-chloro-10,11-dihydrodibenz[b,f][1,4]oxazepine-10-carbonyl)hydrazine.

8. The compound according to claim 1 which is 1-(4-hydroxy-4-phenylpiperidinoacetyl)-2-(8-chloro-10,11-dihydrodibenz[b,f][1,4]oxazepine-10-carbonyl)hydrazine.

9. A compound according to claim 1 of the formula

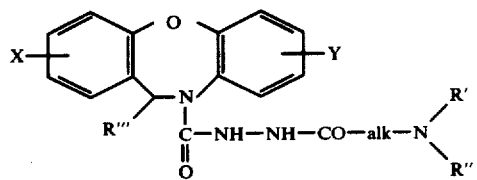

wherein Y represents hydrogen, halogen, lower alkyl having 1-7 carbon atoms, or trifluoromethyl and R''' is lower alkyl having 1-4 carbon atoms.

10. The compound according to claim 1 which is 1-(5-piperidinopentanoyl)-2-(8-chloro-11-methyl-10,11-dihydrodibenz[b,f][1,4]oxazepine-10-carbonyl)hydrazine.